United States Patent
Kamei et al.

(10) Patent No.: US 7,612,051 B2
(45) Date of Patent: Nov. 3, 2009

(54) POWDER COMPOSITION, DISPERSION OF THIS POWDER COMPOSITION IN OIL AND COSMETIC MATERIAL CONTAINING SAME

(75) Inventors: Masanao Kamei, Gumma (JP); Toru Shimizu, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 702 days.

(21) Appl. No.: 10/346,176

(22) Filed: Jan. 17, 2003

(65) Prior Publication Data

US 2003/0185771 A1 Oct. 2, 2003

Related U.S. Application Data

(63) Continuation-in-part of application No. PCT/JP01/06310, filed on Jul. 19, 2001.

(30) Foreign Application Priority Data

Jul. 21, 2000 (JP) ............................... 2000-220892

(51) Int. Cl.
*C07F 7/02* (2006.01)
*A61K 8/18* (2006.01)
*A61K 8/00* (2006.01)
*A61K 8/58* (2006.01)
*A61K 8/27* (2006.01)
*A61K 8/02* (2006.01)
*A61K 31/665* (2006.01)
*A61Q 17/04* (2006.01)
*A61Q 1/02* (2006.01)
*A61Q 1/00* (2006.01)
*A61Q 1/12* (2006.01)
*A61F 2/00* (2006.01)

(52) U.S. Cl. ........................... 514/100; 424/59; 424/63; 424/67; 424/69; 424/401; 424/484; 514/937; 556/400

(58) Field of Classification Search .............. 424/70.12, 424/401, 78.03, 78.02, 59, 60, 63, 67, 69, 424/484; 514/937; 556/400
See application file for complete search history.

(56) References Cited

U.S. PATENT DOCUMENTS 5,362,482 A 11/1994 Yoneyama et al.
6,660,281 B1 * 12/2003 Nakanishi et al. ........... 424/401

FOREIGN PATENT DOCUMENTS

EP 356963 A2 * 3/1990
EP 0953333 11/1999
EP 1065234 1/2001
EP 1291376 3/2003
JP 10316536 * 12/1998
JP 200158926 A * 3/2001

OTHER PUBLICATIONS

Patent Abstracts of Japan, JP10-316536; retrieved on May 10, 2005 from http://www19.ipdl.ncipi.go.jp.*
Derwent abstract, accession No. 1999-257261; abstracting JP 10-316536 (1998).*
Patent Abstract of Japan, JP10-316536; retrieved on May 31, 2005 from West file JPAB (1998).*

* cited by examiner

*Primary Examiner*—Johann R Richter
*Assistant Examiner*—Luke E Karpinski
(74) *Attorney, Agent, or Firm*—Millen, White, Zelano & Branigan, P.C.

(57) ABSTRACT

This invention relates to a powder composition comprising a silicone represented by the following formula (1) comprising an alcoholic hydroxyl group, and a powder, to an oil-based powder composition formed by dispersing this powder composition in an oil, and to a cosmetic material containing these materials.

$$R^1_a R^2_b R^3_c SiO_{(4-a-b-c)/2} \quad (1)$$

where, in formula (1), $R^1$ are identical or different organic groups selected from alkyl groups, aryl, aralkyl or fluorinated alkyl groups having 1-30 carbon atoms, $R^2$ is a substituent having one or more alcoholic hydroxy groups, $R^3$ is a group represented by the following general formula (2),

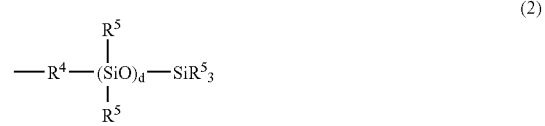

and a, b, c, d are integers satisfying the relations: $1.0 \leq a \leq 2.5$, $0.01 \leq b \leq 1$, $0.001 \leq c \leq 1$, $1.5 \leq a+b+c \leq 2.6$, and $0 \leq d \leq 500$.

The powder composition of this invention has little cohesion, excellent dispersibility and excellent stability over time as an oil-based powder composition. Therefore, cosmetics using these materials have excellent stability in use, and excellent stability over time.

22 Claims, No Drawings

POWDER COMPOSITION, DISPERSION OF THIS POWDER COMPOSITION IN OIL AND COSMETIC MATERIAL CONTAINING SAME

This application is a continuation-in-part of PCT/JP01/06310 filed on Jul. 19, 2001, whose entire disclosure is incorporated by reference herein.

FIELD OF THE INVENTION

This invention relates to a powder composition suitable for cosmetic materials, and in particular to a powder composition having excellent dispersibility comprising alcoholic hydroxyl groups treated by a silicone compound, to a powder composition in oil obtained by dispersing this powder composition in oil, and to a cosmetic material containing these preparations.

BACKGROUND OF THE INVENTION

Untreated powders tend to stick together due to charges and polarity on the powder surface and minute amounts of impurities, and this interferes with the dispersibility and stability of the powder.

Various types of surface treatment have been proposed to improve the dispersibility and stability of the powder, and when used in cosmetics, they improve the "feel" of the product.

The reagents and methods used to treat the powder surface are chosen taking account of properties regarding the nature of the powder surface to be treated and the dispersing medium. For example, there is lipophilic treatment by oils or metal soaps, hydrophilic treatment by surfactants or water-soluble polymers, or water-repellent/oil-repellent treatment by silicone oils.

Among these, silicone compounds which have excellent feel, water repellent properties and stability are becoming increasingly widely used as oils. In order to improve the miscibility of the powder, a surface treatment using methyl hydrogen siloxane has been proposed in Japanese Patent No. 02719303 (Koho), and a surface improvement by a straight chain, single-terminated alkoxy-modified silicone has been proposed in Japanese Patent Application Public Disclosure (Kokai) Hei 7-196946 (Koho). Further, to improve dispersibility in the silicone oil, Japanese Patent Application Public Disclosure (Kokai) Hei 10-167946 (Koho) discloses a method wherein a polyether-modified silicone with a HLB of 2-7 is used as a dispersant.

However, although aggregation and sedimentation were improved in these surface-treated powders, further improvements were still desired. Depending on the treatment agent or treatment method, the powder and treatment agent tended to separate from the cosmetic material, or the powder became lumpy with passage of time and was difficult to re-disperse, so product quality and feel were adversely affected. It was therefore desired to develop a powder composition and powder dispersion with little cohesion, excellent dispersibility and time-dependent stability, and a pleasant feel.

It is therefore a first object of this invention to provide a powder composition having little cohesion and excellent dispersibility.

It is a second object of this invention to provide an oil-based powder having little cohesion and excellent time-dependent stability.

It is a third object of this invention to provide a cosmetic material having excellent usability and good time-dependent stability.

SUMMARY OF THE INVENTION

The above objects of the invention were obtained by a powder composition comprising a silicone represented by the following formula (1) having alcoholic hydroxyl groups and a powder, by an oil-based powder dispersion comprising this powder composition dispersed in an oil, and a cosmetic material comprising these.

(1) In the formula, $R^1$ are organic groups which may be the same or different chosen from alkyl, aryl, aralkyl and fluorine-substituted alkyl groups having 1-30 carbon atoms, $R^2$ is a substituent having one or more alcoholic hydroxyl groups, $R^3$ is a group represented by the following general formula (2),

$R^4$ is an oxygen atom or a bifunctional hydrocarbon group, and a, b, c, d are values satisfying the relations $1.0 \leq a \leq 2.5$, $0.001 \leq b \leq 1$, $0.001 \leq c \leq 1$, $1.5 \leq a+b+c \leq 2.6$, and d is integer of $0 \leq d \leq 500$.

As the powder composition of this invention has excellent dispersibility, it is suitable for cosmetic product applications where usability and time-dependent stability are particularly required. The cosmetic material of this invention comprising the powder composition of this invention not only has an excellent cool feel, but also long-lasting make-up properties and time-dependent stability.

DESCRIPTION OF THE PREFERRED EMBODIMENTS

Specific examples of $R^1$ in the general formula (1), $R^1_a R^2_b R^3_c SiO_{(4-a-b-c)/2}$ are alkyl groups such as methyl, ethyl, propyl, butyl, pentyl, hexyl, heptyl, octyl, nonyl, decyl, cycloalkyl groups such as cyclopentyl and cyclohexyl, aryl groups such as phenyl and tolyl, aralkyl groups such as benzyl and phenetyl, alcohol residues such as oleyloxy and allyloxy, and fluorine-substituted alkyl groups such as trifluoropropyl and heptadecafluorodecyl.

Specific examples of $R^2$ are groups having one OH group such as $-C_3H_6OH$, $-C_4H_8OH$, $-C_8H_{16}OH$ and $-C_{11}H_{22}OH$, groups having two primary alcohols such as

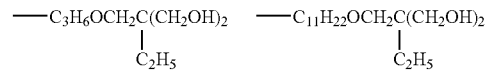

groups having a primary and secondary alcohol such as $C_3H_6OCH_2CH(OH)CH_2OH$, $-C_{11}H_{22}OCH_2CH(OH)CH_2OH$, and groups having two primary alcohols and two secondary alcohols such as

$R^3$ is a group represented by general formulae (6) and (7).

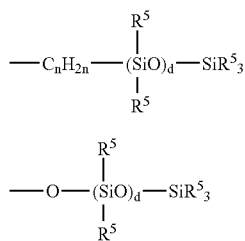

$a$ is 1.0-2.5 but preferably 1.2-2.3, while b and c are 0.001-1.5 but preferably 0.005-1.0, respectively.

$R^5$ in the above formula is identical to $R^1$ or a hydroxyl group.

n is an integer in the range 1-5, and in particular, n synthesized by the reaction of a vinyl group and —SiH group is 2.

d is 0-500, but preferably 1-100. When d is larger than 500, there may be problems such as poor reactivity with the main chain.

The branched silicone which has a group represented by the general formula (6) is synthesized by an addition reaction of an organohydrogen, and a single-terminated vinyl-modified polysiloxane represented by the following general formula (8).

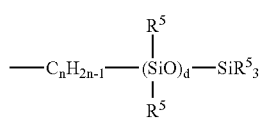

On the other hand, a branched silicone which has a group represented by the general formula (7) is synthesized by an equilibration reaction using an acid or an alkali catalyst according to conventional methods. A branch silicone unit is introduced by using a trialkoxymethylsilane, trihydroxymethylsilane, tris(trimethylsiloxy) methylsilane, and their straight chain or cyclic oligomers for the equilibration reaction. Alternatively, it is possible to perform a ring-opening polymerization by a living polymerization catalyst using a silanol-modified silicone.

There is no particular limitation on the weight average molecular weight of the silicone compound of the above-mentioned general formula (1), when using it as a surface treatment agent for powder, but it is preferably 300-100,000. If 100,000 is exceeded, it will have a tacky feel due to the viscosity of silicone, and if it less than 300, the smoothness of silicone is not obtained. In particular, 1,000-10,000 is preferred.

The silicone compound of the above-mentioned general formula (1) used by this invention is easily synthesized by performing an addition reaction of an organohydrogen polysiloxane and a vinyl group-containing alcohol-modified compound having the following general formula in the presence of a platinum catalyst or a rhodium catalyst.

$$CH_2{=}CHC_nH_{2n}OH \quad CH_2{=}CHC_nH_{2n}OCH_2C(CH_2OH)_2$$
$$\underset{C_2H_5}{|}$$

-continued
$$CH_2{=}CHC_nH_{2n}OCH_2CH(OH)CH_2OH$$

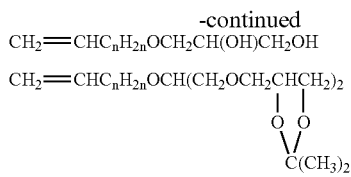

It can also be synthesized by adding the following acetal compound, $CH_2{=}CHC_nH_{2n}OCH$ $(CH_2OCH_2CH(OH)CH_2OH)_2$, and performing a acetone removal reaction.

The organohydrogenpolysiloxane used in these cases may be either straight chain or cyclic, but straight chain is preferred from the viewpoint that the addition reaction proceeds more satisfactorily. Also, there is no particular limitation on the bonding site of the —SiH group, which may be either the side chain or the end of the chain.

It is preferred that the above addition reaction proceeds in the presence of a platinum catalyst or a rhodium catalyst. Specific examples of this catalyst are platinic acid chloride, alcohol-modified platinic acid chloride and platinic acid chloride-vinyl siloxane complex. The amount of catalyst used may be that which is usually employed, but 50 ppm or less and especially 20 ppm or less is preferred in terms of the amount of platinum or rhodium.

The above-mentioned addition reaction may be performed in an organic solvent if needed. Examples of the organic solvent are aliphatic alcohols, such as methanol, ethanol, 2-propanol and butanol, aromatic hydrocarbons, such as toluene and xylene, aliphatic or cycloaliphatic hydrocarbons, such as n-pentane, n-hexane and cyclohexane, and halogenated hydrocarbons, such as dichloromethane, chloroform and carbon tetrachloride. There is no particular limitation on the addition reaction conditions, but the reaction may conveniently be performed under reflux for 1-10 hours.

The powders used by this invention may be any of an inorganic powder, organic powder, surfactant metal salt powder (metal soap), colored pigment, pearl pigment, metal powder pigment, tar coloring matter and natural coloring matter. Examples of inorganic powders are titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lithia mica, silicic acid, silicic acid anhydride, aluminium silicate, magnesium silicate, aluminium magnesium silicate, calcium silicate, barium silicate, strontium silicate, metal salt of tungstic acid, hydroxyapatite, vermiculite, haidilite, bentonite montmorillonite, hectorite, zeolite, ceramic powder, calcium secondary phosphate, alumina, aluminium hydroxide, boron nitride and silica. For use in cosmetic materials, fillers such as mica and sericite, or zinc oxide and titanium dioxide, are preferred.

Examples of organic powders are polyamide powder, polyester powder, polyethylene powder, polypropylene powder, polystyrene powder, polyurethane powder, benzoguanamine powder, polymethyl benzoguanamine powder, poly-tetrafluoroethylene powder, polymethylmethacrylate powder, cellulose powder, silk powder and nylon powder such as 12 nylon powder or 6 nylon powder, styrene acrylic acid copolymer, divinylbenzene-styrene copolymer powder, vinyl resin powder, urea resin powder, phenol resin powder, fluororesin powder, silicon resin powder, acrylate resin powder, melamine resin powder, epoxy resin powder, polycarbonate resin powder, microcrystalline fiber powder, starch and lauroyl lysine powder.

Examples of metal salt powders (metal soaps) are zinc stearate, aluminum stearate, calcium stearate, magnesium stearate, zinc myrisate, magnesium mynrstate, zinc cetyl phospate, calcium cetyl phosphate and zinc sodium cetyl phosphate.

Examples of colored pigments include inorganic red pigments, such as iron oxide, iron hydroxide and iron titanate; inorganic brown pigments, such as gamma-iron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and synthetic resin powder complexes of the inorganic pigments as recited above.

Examples of the pearl pigment include titanium dioxide-coated mica, bismuth oxychloride, titanium dioxide-coated bismuth oxychloride, titanium dioxide-coated talc, fish scale guanine and titanium dioxide-coated colored mica; and examples of the metallic powder pigment include aluminum powder, copper powder and stainless powder.

Examples of tar pigments are Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No.204, Yellow No. 4, Yellow No. 5, Yellow No.202, Yellow No. 203, Yellow No. 204, Green No. 3, Green No. 201, Green No. 204, Green No. 205, Orange No. 201, Orange No. 203, Orange No. 204, Orange No. 206 and Orange No. 207.

The natural pigments described above include powders of carminic acid, laccaic acid, carthamin, bradilin and crocin.

Furthermore, these powders are not particularly restricted as to their shapes (spherical, acicular or tabular), their sizes (smoke particles, fine particles or pigment particles etc.) or their structures (whether they are porous or nonporous), provided that they have so far been used in traditional cosmetic materials.

These powders may be complexed or surface-treated with oils, silicones other than the silicone represented by the above-mentioned general formula (1), or fluorine compounds.

The new silicone powder treatment agent represented by the above-mentioned general formula (1) of this invention can be applied to the powder surface by any known method.

Although the treatment method can be suitably chosen from well-known methods, the following methods may for example be mentioned.

1. The target powder is dispersed in a medium chosen from water or an organic solvent blended with a powder treatment agent.

2. After mixing the powder with the powder treatment agent, surface treatment is performed by crushing the mixture in a ball mill or jet mill.

The oil-based powder of this invention means a dispersion of the powder composition in an oil, or a solution or dispersion of a silicone compound in an oil to which the powder is then added so as to make a mixed dispersion, and it is a liquid dispersion. The oil-based dispersion of this invention may also be suitably modified by known methods such as the methods below.

1. The powder composition obtained as described above may be dispersed in an oil such as an ester oil or silicone oil.

2. A silicone compound is dissolved or dispersed in the oil described above, then the powder is added and mixed by a dispersion device such as a ball mill, bead mill or sand mill.

The oil-based dispersion thus obtained may be blended with a cosmetic material as it is.

When the silicone compound of the general formula (1) in this invention is used as a surface treatment agent for the powder, 0.1-30 weight parts but preferably 0.5-10 weight parts relative to 100 weight parts of the powder is used. Although it depends on the type and form of cosmetic material, the powder composition which has been surface-treated by the above silicone compound is generally blended with the cosmetic materials of this invention so that it is 0.1-99.9 weight parts of the whole cosmetic material.

To the present cosmetic materials, the agents used in general cosmetic materials, such as water, alcohols, water-soluble polymers, a film-forming agent, a surface active agent, an oil-soluble gelling agent, clay modified with organic compounds, resins, powdered materials, ultraviolet absorbents, a moisture retention agent, antiseptics, an antimicrobial agent, perfume, salts, antioxidants, pH regulators, a chelating agent, refrigerant, an anti-inflammatory agent; skin beautifying s, vitamins, amino acids, nucleic acids, hormones and clathrate compounds, can be added so far as they have no adverse influence on the effects of the present invention.

Specific examples of these agelits will now be given, although the invention is not limited thereto.

Examples of alcohols which can be used in this invention are ethanol, propanol, ethylene glycol, ethylene glycol monoalkyl ether, diethylene glycol monoethyl ether, polyethylene glycol, propylene glycol, dipropylene glycol, 1,3-butylene glycol, glycerol, diglycerol, polyglycerol, pentaerythritol, cane sugar, lactose, xylitol, sorbitol, mannitol, maltitol, carrageenan, agar, guar gum, dextrin, tragacanth gum, locust bean gum, polyvinyl alcohol, polyoxyethylene high polymers, polyoxyethylene polyoxypropylene copolymer high polymers, hyaluronic acid, chondroitin sulfate and chitin chitosan, two or more of these being used if necessary. These alcohols are 0.1-99.9% of the weight, but preferably 0.5-50.0% of the weight, of the cosmetic material. At less than 0.1% of the weight, moisture retention properties, antiseptic properties and mildew resistant properties are insufficient, and at more than 99.9% weight, it is impossible to demonstrate the effect of the powder composition of this invention.

The following are examples of oils which can be used in this invention. POE is polyoxyethylene. Natural animal and vegetable fats and oils, and semi-synthetic fats and oils, include avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, methyl caster oil fatty acid, sunflower oil, grape seed oil, bayberry wax, jojoba oil, macadamia nut oil, beeswax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, polyethylene glycol lanolin fatty acid, POE hydrogenated lanolin alcohol ether and egg yolk oil.

Examples of hydrocarbon oils include ozokerite, squalane, squalene, ceresine, paraffin, paraffin wax, liquid paraffin, pristane, polyisobutylene, microcrystalline wax and vaseline.

Examples of higher fatty acids include lauric acid, myristic acid, palmitic acid, stearic acid, behenic acid, undecylenic acid, oleic acid, linoleic acid, linolenic acid, arachidoniacicid, eicosapentaenoic acid (EPA), docosahexaenoic acid (DHA), isostearic acid and 12-hydroxystearic acid.

Examples of higher alcohols which can be added include lauryl alcohol, myristyl alcohol, palmityl alcohol, stearyl alcohol, biphenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of ester oils which can be added include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, neopentyl glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl- palmitate, 2-hexyldecyl palmitate, 2-heptylundecyl palmitate, cholesteryl 12-hydroxystearate, dipentaerythritol fatty acid esters, isopropyl myristate, 2-octyldodecyl myristate, 2-hexyldecyl myristate, myristyl myristate, hexyldecyl dimethyloctanoate, ethyl laurate, hexyl laurate, N-lauroyl-L-glutaminic acid 2-octyldodecyl ester, diisostearyl malic acid, dextrin palmitic acid ester, dextrin stearic acid ester, dextrin 2-ethylhexanoate palmitic acid ester, cane sugar palmitic acid ester, cane sugar stearic acid ester, monobenzylidene sorbitol and dibenzylidene sorbitol.

Examples of glyceride oils include acetoglyceride, diisooctanoic acid glyceride, triisostearic acid glyceride, triisopalmitic acid glyceride, tri-2-ethylhexanoic acid glyceride, monostearic acid glyceride, di-2-heptylundecanoic acid glyceride and trimyristic acid glyceride.

As examples of silicone oils which can be added, mention may be made of dimethylpolysiloxane, methylphenylpolysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane, higher alkoxy-modified silicones such as stearoxysilicone, higher fatty acid-modified silicones, fluorine-modified silicones, amino-modified silicones, alkyl-modified silicones, higher fatty acid ester-modified silicones, silicone resins and silicone rubbers.

As examples of fluorine-containing oils, mention may be made of perfluoropolyether, perfluorodecalin and perfluorooctane.

One, two or more of these oils may be used as necessary. The proportion of these oils in the cosmetic material of this invention may be within a range of 0-90.0 wt %, but it is particularly preferred that the range is 1-90% of weight. If water is used as a component in the composition of the cosmetic material of this invention, the range is 0-99.0% of the weight.

Although an excellent cosmetic material according to this invention may be obtained only using the above-mentioned components, the following components i, ii, iii and iv can also be added if needed.

(i) The Following Powders and/or Colorants

Examples of inorganic powders are titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lithia mica, silicic acid, silicic acid anhydride, aluminium silicate, magnesium silicate, magnesium aluminium silicate, calcium silicate, baium silicate, strontium silicate, metal salts of tangstic acid, hydroxyapatite, vermiculite, haidilite, bentonite, montmorillonite, hectorite, zeolite, ceramic powder, calcium hydrogen phosphate, alumina, aluminium hydroxide, boron nitride and silica.

Examples of organic powders are polyamide powder, polyester powder, polyethylene powder, polypropylene powder, polystyrene powder, polyurethane powder, benzoguanamine powder, polymethyl benzoguanamine powder, poly tetrafluoroethylene powder, polymethylmethacrylate powder, cellulose powder, silk powder, and nylon powder such as 12 nylon and 6 nylon.

Other components that may be added are powders such as styrene acrylic acid copolymer, divinylbenzene, styrene copolymer, vinyl resin, urea resin, phenol resin, fluororesin, silicon resin, acrylate resin, melamine resin, epoxy resin, polycarbonate resin, microcrystalline fiber powder, starch, and lauroyl lysine; surfactant metal salt powders (metal soaps) such as zinc stearate, aluminum stearate, calcium stearate, magnesium stearate, zinc myristate, magnesium myristate, cetyl zinc phosphate, calcium cetyl phosphate, sodium cetyl phosphate; colored pigments including inorganic red pigments such as iron oxide, iron hydroxide iron titanate and □-iron oxide, inorganic yellow pigments such as yellow iron oxide and ocher, inorganic black pigments such as black iron oxide and carbon black, inorganic purple pigments such as manganese violet and cobalt violet, inorganic green pigments such as chromium hydroxide, chromium oxide, cobalt oxide and cobalt titanate, inorganic blue pigments such as Berlin blue and ultramarine blue, lake of tar colorants, lake of natural colorants, and composite powders wherein these powders are complexed; pearl pigments such as titanium dioxide-coated mica, bismuth oxychloride, titanium dioxide-coated bismuth oxychloride, titanium dioxide-coated talc, fish scales foil and titanium dioxide-coated, colored mica; metal powder pigments include aluminium powder, copper powder and stainless steel powder; tar colorants such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; and natural colorants such as carminic acid, laccaic acid, carthamin, bradilin and crocin.

Any other substances may be added if they are normally used in cosmetics regardless of their shape (spherical, acicular, tabular), particle size (smoke particles, fine particles, pigments particles) or particle structure (porous, non-porous).

These powders can also be complexed together, surface-treated with an oil or silicone represented by the above-mentioned general formula (1), or surface-treated with a fluorine compound.

(ii) The Following Surfactants

Saturated or unsaturated fatty acid soaps such as sodium stearate or oleic acid triethanolamine, alkylether carboxylic acid and its salts, carboxylates of condensates of amino acid and fatty acids, amide ether carboxylates, □-sulfo fatty acid ester salts, □-acyl sulfonates, alkylsulfonate salts, alkene sulfonates, sulfonates of fatty acid esters, sulfonates of aliphatic acid amide, alkylsulfonate salts and sulfonates of their formalin condensates, sulfates such as alkyl sulfate esters, secondary higher alcohol sulfuric esters, alkyl and allyl ethereal sulfate esters, sulfuric esters of fatty acid esters, sulfuric esters of aliphatic acid alkyloylamide, Turkey red oil, alkylphosphates, alkenyl phosphates, ether phosphates, alkylarylether phosphates, alkylamide phosphates, N-acylamino acid activators;

cationic surfactants including amines such as alkylamines, polyamines and amino alcohol fatty acid acid derivatives, alkyl quaternary ammonium salts, aromatic quaternary ammonium salts, pyridium salts, imidazolium salts;

nonionic surfactants including sorbitan fatty acid esters, glycerin fatty acid esters, polyglycerol fatty acid esters, propylene glycol fatty acid esters, polyethylene glycol fatty acid esters, cane sugar fatty acid ester, polyoxyethylene alkylethers, poly oxypropylene alkylethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hardening castor oil, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene/alkyl comodified organopolysiloxane, polyoxyelkylene/fluoroalkyl comodified organopolysiloxane, polyoxyalkylene/organo poly siloxane block copolymer, alkanolamide, sugar ether, sugar amide; and ampholytic surfactants such as betaine, aminocarboxylate and imidazolines.

(iii) Crosslinked Organopolysiloxanes

In the cosmetic material of this invention, one, two or more crosslinked organopolysiloxanes can be used depending on the purpose.

The cross-linked organopolysiloxanes suitable for addition to the present cosmetic materials are those which cause swelling when they contain a silicone having a low viscosity of from 0.65-10.0 mm$^2$/sec (25° C.) in a quantity larger than the weight of the cross-linked organopolysiloxanes themselves. And it is preferable that the cross-linked structure of those organopolysiloxanes be formed by the reaction between the hydrogen atoms bonded directly to silicon atoms and a cross-linking agent having at least two vinylic reactive moieties per molecule. In the cross-linking reaction, it is appropriate to use the cross-linking agent containing at least one moiety selected from polyoxyalkylene, alkyl, alkenyl, aryl or fluoroalkyl moieties. The suitable proportion of such cross-linked organopolysiloxanes mixed in the present cosmetic material is from 0.1-30.0 wt %, but preferably from 1.0-10.0 wt %, to the total weight of the cosmetic material.

(iv) Silicone Resins such as Acryl/Silicone Graft or Block Copolymer, and Silicone Compounds Having a Reticular Structure The present cosmetic material can further contain one or more of silicone resins such as acryl-silicone graft or block copolymers and silicone compounds having a reticular structure, if needed.

In particular, acrylsilicone resins are suitable for the present cosmetic materials. Further, it is desirable that at least one moiety selected from the group consisting of pyrrolidone, long-chain alkyl, polyoxyalkylene and fluoroalkyl moieties be present in such an acrylsilicone resin molecule. Further, it is appropriate for those silicone resins to be reticular silicone compounds. When the silicone resins, such as acryl-silicone graft or block copolymer and silicone compounds having a reticular structure, are mixed in the present cosmetic material, the appropriate proportion of silicone resins is from 0.1-20 wt %, but preferably from 1-10 wt %, to the total weight of the cosmetic material.

There is no particular limitation on the applications of the cosmetic material of this invention, but suitable examples which can be mentioned are skin care products, hair products, antiperspirants, makeup products and ultra-violet light protection products. In addition, there is no particular limitation on the form of the product, but it may be in the form of a liquid, emulsion, cream, solid, paste, gel, powder, laminate, mousse or spray.

Hereafter, this invention will be described in more detail by means of specific examples, but it is not to be construed as being limited thereby.

Unless otherwise specified, "part" means "weight part" and "%" means "wt %." Viscosities are given at 25° C.

Manufacturing Example 1

187 weight parts of an organohydrogen siloxane shown by the following average empirical formula (8), 100 weight parts of isopropyl alcohol and 18.3 weight parts of trimethylol propane monoallyl ether shown by the following general formula (9) were introduced into a reactor, 2 parts of an isopropyl alcohol solution containing 0.5 wt % of chloroplatinic acids was added, and a reaction was performed under reflux of the solvent for 6 hours.

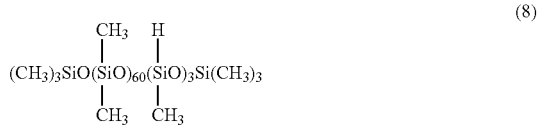

(8)

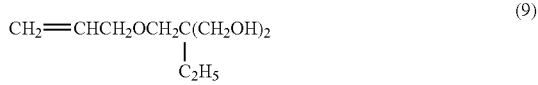

(9)

The reactant was heated under reduced pressure to distil off the solvent, and the organopolysiloxane shown by the following average empirical formula (10) was thus obtained.

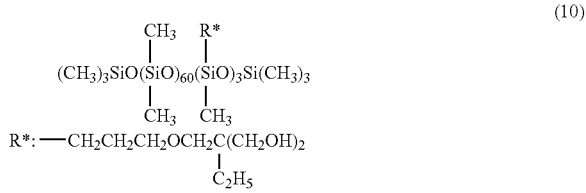

(10)

The reaction product was a light brown, transparent liquid, and its viscosity was 200 mm$^2$/second (25° C.)

Manufacturing Example 2

186 weight parts of an organohydrogen siloxane shown by the following average empirical formula (8) used in Example 1, 100 weight parts of isopropyl alcohol and 24.3 weight parts of the compound shown by the general formula (11) were introduced into a reactor, 2 parts of an isopropyl alcohol solution containing 0.5 wt % of chloroplatinic acids was added, and a reaction was performed under reflux of the solvent for 6 hours.

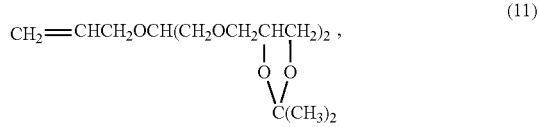  (11)

100 g of 0.025N hydrochloric acid was added, and a acetone removal reaction was performed under reflux of the solvent for 6 hours.

The reactant was heated under reduced pressure to distil off the solvent, and the organopolysiloxane shown by the following average empirical formula (12) was thus obtained.

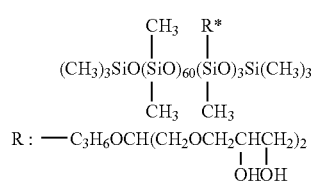  (12)

The reaction product was a light brown, transparent liquid, and its viscosity was 1200 mm$^2$/second (25° C).

Manufacturing Example 3

460 weight parts of an organohydrogen siloxane shown by the following average empirical formula (13), 500 weight parts of isopropyl alcohol and 19.6 weight parts of trimethylol propane ether shown by the general formula (9) were introduced into a reactor, 2 parts of an isopropyl alcohol solution containing 0.5 wt % of chloroplatinic acid was added, and a reaction was performed under reflux of the solvent for 6 hours.

  (13)

The reactant was heated under reduced pressure to distil off the solvent, and the organopolysiloxane shown by the following average empirical formula (14) was thus obtained.

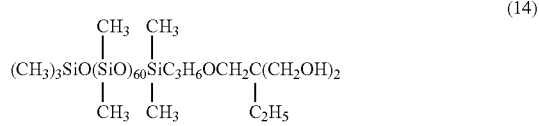  (14)

The reaction product was a light brown, transparent liquid, and its viscosity was 120 mm$^2$/second (25° C.).

Manufacturing Example 4

460 weight parts of an organohydrogen siloxane shown by the following average empirical formula (13) used in Example 3, 500 weight parts of isopropyl alcohol and 45 weight parts of trimethylol propane monoallyl ether shown by the following general formula (9) used in Example 2 were introduced into a reactor, 2 parts of an isopropyl alcohol solution containing 0.5 wt % of chloroplatinic acid was added, and a reaction was performed under reflux of the solvent for 6 hours. 100 g of 0.025N hydrochloric acid was added, and a acetone removal reaction was performed under reflux of the solvent for 6 hours.

The reactant was heated under reduced pressure to distil off the solvent, and the organopolysiloxane shown by the following average empirical formula (15) was thus obtained.

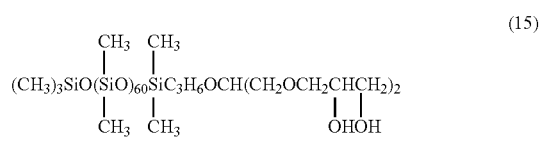  (15)

The reaction product was a light brown, transparent liquid, and its viscosity was 350 mm$^2$/second (25° C.).

(Manufacturing Example) 5

478 weight parts of an organohydrogen siloxane shown by the following average empirical formula (8) used in Example 1, 300 weight parts of isopropyl alcohol, 16.4 weight parts of a trimethylol propane monoallyl compound ether shown by the general formula (9) used in Example 1, and 301 weight parts of the single terminated vinyl-modified silicone having the following average empirical formula (16) were introduced into a reactor, 2 parts of a 0.5% isopropyl alcohol solution of chloroplatinic acid was added, and a reaction performed under reflux for 6 hours.

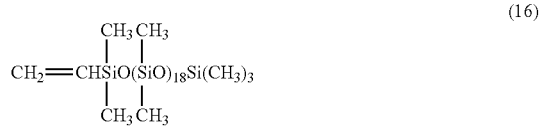  (16)

The reaction product was heated under reduced pressure to distil off the solvent, and the organopolysiloxane shown by the following average empirical formula (17) was thereby obtained.

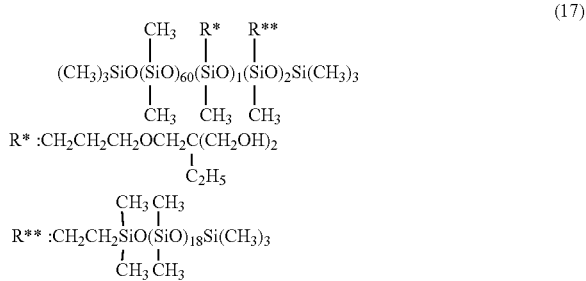  (17)

The product was a light brown, transparent liquid, and its viscosity 1200 cs (25° C.).

(Manufacturing Example) 6

478 weight parts of an organohydrogen siloxane shown by the following average empirical formula (8) used in Example 1, 300 weight parts of isopropyl alcohol, 86.6 weight parts of the compound represented by the aforesaid general formula (11) used in Example 2, and 151 weight parts of the compound having the aforesaid average empirical formula (16) were introduced into a reactor, 2 parts of a 0.5% isopropyl alcohol solution of chloroplatinic acid was added, and a reaction performed under reflux for 6 hours.

100 g 0.025N hydrochloric acid was added, and a de-acetone reaction performed under reflux for 6 hours.

The reaction product was heated under reduced pressure to distil off the solvent, and the organopolysiloxane shown by the following average empirical formula (18) was thereby obtained.

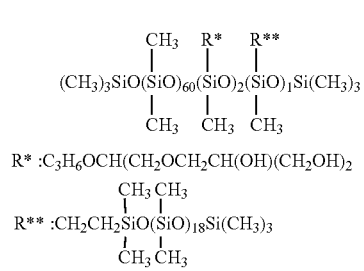

(18)

$R^*$ : $C_3H_6OCH(CH_2OCH_2CH(OH)(CH_2OH)_2$ $R^{**}$ : $CH_2CH_2\underset{CH_3}{\overset{CH_3}{Si}}O(SiO)_{18}Si(CH_3)_3$
$\phantom{R^{**}:CH_2CH_2Si}\overset{|}{CH_3}\phantom{O(SiO)}\overset{|}{CH_3}$ This product was a light brown, transparent liquid, and its viscosity was 11000 cs (25° C.).

(Manufactured Example) 7

272 weight parts of the organohydrogen siloxane represented by the following average empirical formula (19),

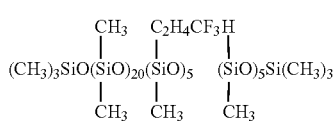

(19)

200 weight parts of isopropyl alcohol, 49 weight parts of the compound having the aforesaid general formula (9) and 301 weight parts of the aforesaid compound having the average empirical formula (16), were introduced into a reactor, 2 parts of a 0.5% isopropyl alcohol solution of chloroplatinic acid was added, and a reaction performed under reflux for 6 hours.

The reaction product was heated under reduced pressure to distil off the solvent, and the organopolysiloxane shown by the following average empirical formula (20) was thereby obtained.

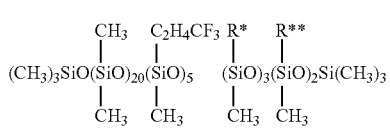

(20)

-continued $R^*$ : $CH_2CH_2CH_2OCH_2\underset{\overset{|}{C_2H_5}}{C}(CH_2OH)_2$ $R^{**}$ : $CH_2CH_2\underset{CH_3}{\overset{CH_3}{Si}}O(SiO)_{18}Si(CH_3)_3$
$\phantom{R^{**}:CH_2CH_2Si}\overset{|}{CH_3}\phantom{O(SiO)}\overset{|}{CH_3}$ This product was a light brown, transparent liquid, and its viscosity was 750 cs (25° C.).

MANUFACTURING EXAMPLE 8

272 weight parts of the organohydrogen siloxane represented by the above average empirical formula (20), 500 weight parts of isopropyl alcohol, 17 weight parts of propenyl alcohol and 153 weight parts of a compound having the following empirical formula (21):

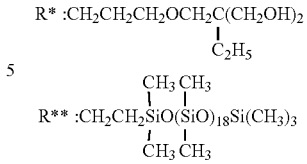

(21)

were introduced into a reactor, 2 parts of a 0.5% isopropyl alcohol solution of chloroplatinic acid was added, and a reaction performed under reflux for 6 hours.

The reaction product was heated under reduced pressure to distil off the solvent, and the organopolysiloxane shown by the following average empirical formula (22) was thereby obtained.

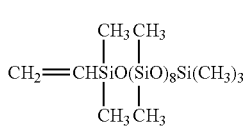

(22)

$R^*$ : $CH_2CH_2CH_2OH$ $R^{**}$ : $CH_2CH_2\underset{CH_3}{\overset{CH_3}{Si}}O(SiO)_8Si(CH_3)_3$
$\phantom{R^{**}:CH_2CH_2Si}\overset{|}{CH_3}\phantom{O(SiO)}\overset{|}{CH_3}$ This product was a light brown, transparent liquid, and its viscosity was 260 cs (25° C.).

EXAMPLES

Example 1

10 g of the silicone compound obtained in Manufacturing Example 1 was dissolved in 50 g decamethylcyclopentasiloxane, 40 g of titanium dioxide (TTO—S-2: Ishihara Sangyo Ltd.) was dispersed therein using a bead mill, and a titanium dioxide dispersion (A) was thus obtained.

Example 2

8 g of the silicone compound obtained in Manufacturing Example 2 was dissolved in 42 g decamethylcyclopentasiloxane, 50 g of zinc oxide (ZnO350: Osaka Sumitomo Cement Ltd.) was dispersed therein using a bead mill, and a zinc oxide dispersion (B) was thus obtained.

Example 3

10 g of the silicone compound obtained in Manufacturing Example 3 was dissolved in 40 g decamethylcyclopentasiloxane, 50 g of zinc oxide (ZnO350: Osaka Sumitomo Cement Ltd.) was dispersed therein using a bead mill, and a zinc oxide dispersion (C) was thus obtained.

Example 4

8 g of the silicone compound obtained in Manufacturing Example 4 was dissolved in 52 g decamethylcyclopentasiloxane, 40 g of titanium dioxide (ITO—S-2: Ishihara Sangyo Ltd.) was dispersed therein using a bead mill, and a titanium dioxide dispersion (D) was thus obtained.

Example 5

10 g of the silicone compound obtained in Manufacturing Example 5 was dissolved in 50 g decamethylcyclopentasiloxane, 40 g of titanium dioxide (TTO—S-2: Ishihara Sangyo Ltd.) was dispersed therein using a bead mill, and a titanium dioxide dispersion (E) was thus obtained.

Example 6

8 g of the silicone compound obtained in Manufacturing Example 6 was dissolved in 42 g decamethylcyclopentasiloxane, 50 g of zinc oxide (ZnO350, Osaka Sumitomo Cement Ltd.) was dispersed therein using a bead mill, and a zinc oxide dispersion (F) was thus obtained.

Example 7

10 g of the silicone compound obtained in Manufacturing Example 7 was dissolved in 40 g decamnethylcyclopentasiloxane, 50 g of zinc oxide (ZnO350, Osaka Sumitomo Cement Ltd.) was dispersed therein using a bead mill, and a zinc oxide dispersion (G) was thus obtained.

Example 8

8 g of the silicone compound obtained in Manufacturing Example 8 was dissolved in 52 g decamethylcyclopentasiloxane, 40 g of titanium dioxide (TTO—S-2: Ishihara Sangyo Ltd.) was dispersed therein using a bead mill, and a titanium dioxide dispersion (H) was thus obtained.

Comparative Example 1

10 g of a polyether-modified silicone compound (KF6017, Shin-Etsu Chemical Industries) was dissolved in 50 g decamethylcyclopentasiloxane, 50 g of zinc oxide (ZnO350: Osaka Sumitomo Cement Ltd.) was dispersed therein using a bead mill, and a zinc oxide dispersion (I) was thus obtained.

Comparative Example 2

5 g of methyl hydrogen polysiloxane (KF99, Shin-Etsu Chemical Industries Ltd.) was dissolved in isopropyl alcohol, sprayed into 40 g of titanium dioxide (TTO—S-2: Ishihara Sangyo Ltd.), and then dried at 100° C. The product was added to 60 g of decamethylcyclopentasiloxane, dispersed therein using a bead mill, and a titanium dioxide dispersion (J) was thus obtained.

Example 9

5 g of the silicone compound obtained in Manufacturing Example 1 was dissolved in isopropyl alcohol, 40 g of titanium dioxide (TTO—S-1, Ishihara Sangyo Ltd.) was dispersed therein, the solvent was distilled off, and a titanium dioxide composition (K) was thus obtained.

Example 10

5 g of the silicone compound obtained in Manufacturing Example 2 was dissolved in isopropyl alcohol, 50 g of zinc oxide (ZnO 350, Osaka Sumitomo Cement Ltd.) was dispersed therein, the solvent was distilled off, and a zinc oxide composition (L) was thus obtained.

Example 11

8 g of the silicone compound obtained in Manufacturing Example 3 was dissolved in isopropyl alcohol, 50 g of zinc oxide (ZnO 350, Osaka Sumitomo Cement Ltd.) was dispersed therein, the solvent was distilled off, and a zinc oxide composition (M) was thus obtained.

Example 12

10 g of the silicone compound obtained in Manufacturing Example 4 was dissolved in isopropyl alcohol, 40 g of titanium dioxide (TTO—S-1, Ishihara Sangyo Ltd.) was dispersed therein, the solvent was distilled off, and a titanium dioxide composition (N) was thus obtained.

Example 13

5 g of the silicone compound obtained in Manufacturing Example 5 was dissolved in isopropyl alcohol, 40 g of titanium dioxide (TTO—S-1, Ishihara Sangyo Ltd.) was dispersed therein, the solvent was distilled off, and a titanium dioxide composition (O) was thus obtained.

Example 14

5g of the silicone compound obtained in Manufacturing Example 6 was dissolved in isopropyl alcohol, 50 g of zinc oxide (ZnO350, Osaka Sumitomo Cement Ltd.) was dispersed therein, the solvent was distilled off, and a zinc oxide composition (P) was thus obtained.

Example 15

8 g of the silicone compound obtained in Manufacturing Example 7 was dissolved in isopropyl alcohol, 50 g of zinc oxide (ZnO350, Osaka Sumitomo Cement Ltd.) was dispersed therein, the solvent was distilled off, and a zinc oxide composition (Q) was thus obtained.

Example 16

10 g of the silicone compound obtained in Manufacturing Example 8 was dissolved in isopropyl alcohol, 40 g of titanium dioxide (TTO—S-1, Ishihara Sangyo Ltd.) was dispersed therein, the solvent was distilled off, and a titanium dioxide composition (R) was thus obtained.

Comparative Example 3

10 g of a polyether-modified silicone compound (KF6017, Shin-Etsu Chemical Industries) was dissolved in 50 g isopropyl alcohol, 50 g of titanium dioxide (ZnO350: Osaka Sumitomo Cement Ltd.) was dispersed therein using a bead mill, and the solvent was distilled off to obtain a titanium dioxide dispersion (S).

Comparative Example 4

5 g of methyl hydrogen polysiloxane (KF99, Shin-Etsu Chemical Industries Ltd.) was dissolved in isopropyl alcohol, 50 g of titanium dioxide C(TTO—S-2: Ishihara Sangyo Ltd.) was added, and the solvent was distilled off to obtain a titanium dioxide dispersion (T).

Dispersibility

The powder compositions and oil-based dispersions in Examples 1 to 16 and Comparative Examples 1 to 4, were mixed with dimethylcyclopentanesiloxane so that the concentration was 5%, the mixed solution was placed in a 50 ml sedimentation tube, and the sedimentation volume was visually observed after two days. The results are shown in the following table.

|  | Sedimentation volume (%) |
|---|---|
| Example 1 | 0.5 |
| Example 2 | 0.7 |
| Example 3 | 0.5 |
| Example 4 | 0.4 |
| Example 5 | 0.6 |
| Example 6 | 0.7 |
| Example 7 | 0.5 |
| Example 8 | 0.6 |
| Example 9 | 0.2 |
| Examnle 10 | 0.7 |
| Example 11 | 0.6 |
| Example 12 | 0.5 |
| Example 13 | 0.4 |
| Example 14 | 0.7 |
| Example 15 | 0.6 |
| Example 16 | 0.4 |
| Comparative Example 1 | 6.5 |
| Comparative Example 2 | 10.2 |
| Comparative Example 3 | 9.3 |
| Comnarative Examule 4 | 15.3 |

As can be seen from the above table, in the case of Examples 1-16, the mixture was homogenous without sedimentation, and dispersibility was good. However, in the case of Comparative Examples 1-4, the mixture was not homogeneous and sedimented out.

A sunscreen having the composition in Table 1 or Table 2 below was prepared, and its quality was evaluated. The unit is "part".

Preparation of Sunscreen

Examples 17 to 24, and Comparative Example 5

A: 1, 2, 3, 4 were mixed uniformly.
B: 6, 7, 9 were mixed uniformly.
C: B was added to A, and emulsified.
D: 5, 10 and any of 11-19 were added to C to obtain a sunscreen.

Table 1

TABLE 1

|  | | Examples | | | | | | | | Compar. Examples |
|---|---|---|---|---|---|---|---|---|---|---|
|  | | 17 | 18 | 19 | 20 | 21 | 22 | 23 | 24 | 5 |
| 1 | KF96 6cs | 5.0 | 5.0 | 5.0 | 5.0 | 5.0 | 5.0 | 5.0 | 5.0 | 5.0 |
| 2 | KSG-21 | 5.0 | 5.0 | 5.0 | 5.0 | 5.0 | 5.0 | 5.0 | 5.0 | 5.0 |
| 3 | Triisooctanoic acid glyceryl | 3.0 | 3.0 | 3.0 | 3.0 | 3.0 | 3.0 | 3.0 | 3.0 | 3.0 |
| 4 | kF-6017 | 1.0 | 1.0 | 1.0 | 1.0 | 1.0 | 1.0 | 1.0 | 1.0 | 1.0 |
| 5 | Octylmethoxycinnamic acid | 6.0 | 6.0 | 6.0 | 6.0 | 6.0 | 6.0 | 6.0 | 6.0 | 6.0 |
| 6 | Sodium chloride | 0.5 | 0.5 | 0.5 | 0.5 | 0.5 | 0.5 | 0.5 | 0.5 | 0.5 |
| 7 | 1,3 butylene glycol | 2.0 | 2.0 | 2.0 | 2.0 | 2.0 | 2.0 | 2.0 | 2.0 | 2.0 |
| 8 | Decamethylcyclopentasloxane | — | — | — | — | 30 | 25 | 30 | 30 | — |
| 9 | Purified water - remainder | Residual amount | Residual amount | Residual amount | Residual amount | Residual amount | Residual amount | Residual amount | Residual amount | Residual amount |
| 10. | Perfume - suitable amount | Suitable amount | Suitable amount | Suitable amount | Suitable amount | Suitable amount | Suitable amount | Suitable amount | Suitable amount | Suitable amount |
| 11. | Titanium oxide dispersion (A) (Example 1) | 50 | | | | | | | | |
| 12. | Zinc oxide dispersion (B) (Example 2) | | 50 | | | | | | | |
| 13. | Zinc oxide dispersion (C) (Example 3) | | | 50 | | | | | | |
| 14. | Titanium dioxide dispersion (D) (Example 4) | | | | 50 | | | | | |
| 15. | Titanium dioxide composition (E) (Example 5) | | | | | 50 | | | | |
| 16. | Zinc oxide composition (F) (Example 6) | | | | | | 50 | | | |
| 17. | Zinc oxide composition (G) (Example 7) | | | | | | | 50 | | |

TABLE 1-continued

|  | Examples | | | | | | | | Compar. Examples |
|---|---|---|---|---|---|---|---|---|---|
|  | 17 | 18 | 19 | 20 | 21 | 22 | 23 | 24 | 5 |
| 18. Titanium dioxide composition (H) (Example 8) |  |  |  |  |  |  |  | 50 |  |
| 19. Zinc oxide dispersion (1) (Compar, Example 1) |  |  |  |  |  |  |  |  | 50 |
| Test results |  |  |  |  |  |  |  |  |  |
| 1. Dispersion stability | ◎ | ◎ | ◎ | ◎ | ◎ | ◎ | ◎ | ◎ | ○ |
| 2. Feel in usage smoothness | ◎ | ◎ | ◎ | ◎ | ◎ | ◎ | ◎ | ◎ | ○ |
| spreadability | ◎ | ◎ | ◎ | ◎ | ◎ | ◎ | ◎ | ◎ | Δ |
| transparency of cosmetic film | ◎ | ◎ | ◎ | ◎ | ○ | ◎ | ◎ | ○ | Δ |
| absence of tackiness | ◎ | ◎ | ◎ | ◎ | ◎ | ◎ | ◎ | ◎ | ○ |
| sunscreen effect | ◎ | ◎ | ◎ | ◎ | ◎ | ◎ | ○ | ○ | ○ |

KF.96: dimethylpolysiloxane
KSG-21: silicone gel
KF-6017: polyether silicone (Shin-Etsu Chemical Co., Ltd.)

Examples 25 to 32, and Comparative Example 6

A: 1, 2, 3, 4 were mixed uniformly, and 8, 10 and any of 20-28 were added to obtain a sunscreen.
B: 6, 7, 9 were mixed uniformly.
C: B was added to A, and emulsified.
D: 5 was added to C to obtain a sunscreen.

The quality of the sunscreens having the compositions in Table 2 were evaluated as follows.

TABLE 2

|  | Examples | | | | | | | | Compar. Examples |
|---|---|---|---|---|---|---|---|---|---|
|  | 25 | 26 | 27 | 28 | 29 | 30 | 31 | 32 | 6 |
| 1. KF96 6cs | 5.0 | 5.0 | 5.0 | 5.0 | 5.0 | 5.0 | 5.0 | 5.0 | 5.0 |
| 2. KSG-21 | 5.0 | 5.0 | 5.0 | 5.0 | 5.0 | 5.0 | 5.0 | 5.0 | 5.0 |
| 3. Triisoctanoic acid glyceryl | 3.0 | 3.0 | 3.0 | 3.0 | 3.0 | 3.0 | 3.0 | 3.0 | 3.0 |
| 4 KF-6017 | 3.0 | 4.0 | 1.0 | 1.0 | 1.0 | 1.0 | 1.0 | 1.0 | 1.0 |
| 5. Octylmethoxycinnamic acid | 6.0 | 6.0 | 6.0 | 6.0 | 6.0 | 6.0 | 6.0 | 6.0 | 6.0 |
| 6. Sodium chloride | 3.5 | 0.5 | 0.5 | 0.5 | 0.5 | 0.5 | 0.5 | 0.5 | 0.5 |
| 7. 1,3 butylene glycol | 4.0 | 5.0 | 2.0 | 2.0 | 2.0 | 2.0 | 2.0 | 2.0 | 2.0 |
| 8. Decamethylcyclopentasiloxane | 30 | 25 | 30 | 30 | 30 | 25 | 30 | 30 | 25 |
| 9. Purified water - remainder | Residual amount | Residual amount | Residual amount | Residual amount | Residual amount | Residual amount | Residual amount | Residual amount | Residual amount |
| 10. Perfume - suitable amount | Suitable amount | Suitable amount | Suitable amount | Suitable amount | Suitable amount | Suitable amount | Suitable amount | Suitable amount | Suitable amount |
| 20. Titanium dioxide dispersion (K) (Example 9) | 50 |  |  |  |  |  |  |  |  |
| 21. Zinc oxide dispersion (L) (Example 10) |  | 50 |  |  |  |  |  |  |  |
| 22. Zinc oxide dispersion (M) (Example 11) |  |  | 50 |  |  |  |  |  |  |
| 23. Titanium dioxide dispersion (N) (Example 12) |  |  |  | 50 |  |  |  |  |  |
| 24. Titanium dioxide composition (O) (Example 13) |  |  |  |  | 20 |  |  |  |  |
| 25. Zinc oxide composition (P) (Example 14) |  |  |  |  | 25 |  |  |  |  |
| 26. Zinc oxide composition (Q) (Example 15) |  |  |  |  |  | 20 |  |  |  |
| 27. Titanium dioxide composition (R) (Example 16) |  |  |  |  |  |  | 20 |  |  |
| 28. Zinc oxide dispersion (T) (Compar. Example 4) |  |  |  |  |  |  |  |  | 25 |
| Test result |  |  |  |  |  |  |  |  |  |
| 1. Dispersion stability | ◎ | ◎ | ◎ | ◎ | ◎ | ◎ | ◎ | ◎ | Δ |
| 2. Feel in usage smoothness | ◎ | ◎ | ◎ | ◎ | ◎ | ◎ | ◎ | ◎ | ○ |
| spreadability | ◎ | ◎ | ◎ | ◎ | ◎ | ◎ | ◎ | ◎ | Δ |

TABLE 2-continued

|  | Examples | | | | | | | | Compar. Examples |
|---|---|---|---|---|---|---|---|---|---|
|  | 25 | 26 | 27 | 28 | 29 | 30 | 31 | 32 | 6 |
| transparency of cosmetic film | ◎ | ◎ | ◎ | ◎ | ○ | ◎ | ◎ | ○ | Δ |
| absence of tackiness | ◎ | ◎ | ◎ | ◎ | ◎ | ◎ | ◎ | ◎ | ○ |
| sunscreen effect | ◎ | ◎ | ◎ | ◎ | ◎ | ◎ | ○ | ○ | ○ |

KF-96: dimethylpolysiloxane
KSG-21: silicone gel
KF-6017: polyether silicone (Shin-Etsu Chemical Co., Ltd.)

1. Dispersion Stability of Powder

After leaving the sunscreen at room temperature for 1 month, the aggregation of the powder was observed and evaluated according to the following criteria.

Evaluation Criteria
◎: Aggregation of powder is not observed
○: Slight aggregation of powder is observed
Δ: Tendency of powder to aggregate is observed:
x: Aggregation of powder is clearly observed 2. Performance Evaluation 50 female panelists evaluated the sunscreen obtained with regard to smoothness, extendability, transparency of cosmetic film, stickiness on the skin and sunscreen effect, on a 5 point scale. The average points obtained were classed as ◎, ○, Δ or x according to the following criteria for each example.

Evaluation Criteria
5 points good
4 points fairly good
3 points normal
2 points rather poor
1 points poor Evaluation of Average Points:
Average points obtained 4.5 or more: ◎
Average points obtained 3.5 to 4.5: ○
Average points obtained 2.5 to 3.5: Δ
Average points obtained 1.5 to 2.5: x As can be seen from the results of the above table, the sunscreens of Examples 17-32 showed no aggregation of the powder and excellent dispersibility. In addition, they all felt pleasant to use. On the other hand, in Comparative Examples 5 and 6 with added polyether silicone, a small amount of aggregation was observed in the powder, the cosmetic film had poor transparency, and it did not feel good enough to use.

Example 33

Eyeliner

| (Component) | (%) |
|---|---|
| 1. Decamethylcyclopentasloxane | 45.0 |
| 2. Polyether-modified siloxane (Note 1) | 3.0 |
| 3. Organosilicon resin | 15.0 |
| 4. Dioctadecyldimethylammmonium-modified montmorillonite | 3.0 |
| 5. Black iron oxide treated with silicone obtained in Manufacturing Example 3 | 10.0 |
| 6. 1,3-butylene glycol | 5.0 |
| 7. Sodium dehydroacetate | Suitable amount |
| 8. Antiseptic | Suitable amount |
| 9. Perfume | Suitable amount |
| 10. Purified water | Residual amount |

(Note 1)
Polyether-modified silicone; KF-6017 (Shin-Etsu Chemical Co., Ltd.)
(Manufacturing Method)

A: Components 1-4 were mixed, and Component 5 was added to give a uniform dispersion.

B: Components 6-8 and 10 were mixed.

C: B was gradually added to A, and Component 9 was added to obtain an eyeliner.

The eyeliner obtained above spread lightly, was easy to draw with, and had a cool, cool freshness without any tackiness. It did not change with temperature or time, was extremely easy to use and very stable, had excellent water resistance and perspiration resistance, and lasted a very long time.

| (Component) | (%) |
|---|---|
| 1. Decamethyl cyclopentasioxane | 8.3 |
| 2. Dimethylpolysiloxane (6 mm$^2$/second) | 5.0 |
| 3. Polyether-modified silicone (Note 1) | 2.0 |
| 4. Dioctadecyldimethylammmonium-modified montmorillonite | 4.0 |
| 5. Powder dispersion (Note 2) | 61.3 |
| 6. Dipropylene glycol | 5.0 |
| 7. Para-oxybenzoic acid methyl ester | 0.3 |
| 8. 2-amino-2-methyl-1,3-propanediol | 0.2 |
| 9. Hydrochloric acid | 0.1 |
| 10. Perfume | Suitable amount |
| 11. Wate | Residual amount |

(Note 1)
Polyether-modified silicone: KF-6017 (Shin-Etsu Chemical Co., Ltd.)
(Note 2)
| Titanium dioxide | 15% |
| Talc | 9% |
| Mica | 9% |
| Red ocher | 2.4% |
| Yellow iron oxide | 1.0% |
| Black iron oxide | 0.3% |
| Silicone compound obtained in Manufacturing Example 2 | 10% |
| Powder dispersion obtained by dispersing decamethylpentasiloxane by a ball mill. | 53.3% |

(Manufacturing Method)

A: Components 1-4 were heated and mixed, Component 5 was added and the mixture made homogeneous.

B: Components 6-9 and 11 were added and dissolved (pH of aqueous system was 9.0)

C: B was gradually added to A with stirring to make an emulsion, cooled, and Component 10 was added to obtain an emulsion.

The foundation obtained above had a fine texture, spread lightly, was non-tacky and non-oily, moist, fresh and clean. It lasted well, did not change with temperature or time, and was extremely stable.

Example 35

Eye Shadow

| (Components) | (%) |
|---|---|
| 1. Decamethyl cyclopentasiloxane | 15.0 |
| 2. Dimethylpolysiloxane (6 mm$^{2/second}$) | 10.0 |
| 3. Polyether modified silicone (Note 1) | 2.0 |
| 4. PEG (10) lauryl ether (Note 2) | 0.5 |
| 5. Chromium oxide treated by silicone compound obtained in Manufacturing Example 3 | 6.2 |
| 6. Permanent blue treated by silicone compound obtained in Manufacturing Example 3 | 4.0 |
| 7. Titanium-coated mica treated by silicone compound obtained in Manufacturing Example 3 | 6.0 |
| 8. Sodium chloride | 2.0 |
| 9. Propylene glycol | 8.0 |
| 10. Antiseptic | Suitable amount |
| 11. Perfume | Suitable amount |
| 12. Purified water | Residual amount |

(Note 1)
Polyoxyalkylene/alkyl co-modified organopoly sioxane: KF6026 (Shin-Etsu Chemical Co.,Ltd.)
(Note 2)
PEG (10) means that ten polyethylene glycol units are joined together.

(Manufacturing Method)
A: Components 1-4 were mixed, and Components 5-7 were added and uniformly dispersed.
B: Components 8-10 and 12 were dissolved uniformly.
C: B was gradually added to A with stirring to form an emulsion, and Component 11 was added to obtain an eye shadow.

The eye shadow obtained above spread lightly, was not oily or powdery, and had a fresh, non-tackiness. It had excellent water resistance, water repellence and perspiration resistance, lasted well, did not disintegrate when used in cosmetics, did not change with temperature or time and was very stable.

Example 36

Liquid Emulsion Foundation

| (Components) | (%) |
|---|---|
| 1. Dimethylpolysiloxane (6 mm$^2$/second) | 5.0 |
| 2. Mulberry orchid | 4.0 |
| 3. Dioctanoic acid neopentyl glycol | 3.0 |
| 4. Myristic acid isosteairic acid diglycerate | 2.0 |
| 5. α-mono isostearyl glyceryl ether | 1.0 |
| 6. Polyether-modified silicone (Note 1) | 1.0 |
| 7. Aluminium distearate | 0.2 |
| 8. Powder dispersion (Note 2) | 26.2 |
| 9. Magnesium sulfate | 0.7 |
| 10. Glycerin | 3.0 |
| 11. Antiseptic | Suitable amount |
| 12. Perfume | Suitable amount |
| 13. Purified water | Residual amount |

(Note 1)
Polyoxyalkylene/alkyl co-modified organopoly siloxane: KF6026 (Shin-Etsu Chemical Co., Ltd.):
(Note 2)
Powder dispersion obtained by dispersing the following components in a bead mill

| (Components) | (%) |
|---|---|
| Titanium dioxide | 20 |
| Sericite | 8 |
| Talc | 12 |
| Red ocher | 1.6 |
| Black iron oxide | 0.4 |
| Silicone compound that was obtained in Manufacturing Example 4 | 10 |
| Decamethylcyclopentasiloxane | 48.0 |

(Manufacturing Example)
A: Components 1-7, 10 were heated with mixing, Component 8 was added and blended uniformly.

B: Components 9 to 11 and 13 were heated and dissolved.

C: B was gradually added to A with stirring to make an emulsion, cooled, and Component 12 was added to obtain a liquid emulsion foundation.

The liquid emulsion foundation obtained above had a low viscosity and fine texture, spread lightly, was non-tacky and non-oily, moist, fresh and had a cool freshness. It lasted a long time, did not change with temperature or time, and was extremely stable.

Example 37

Cream

| (Components) | (%) |
|---|---|
| 1. Dimethylpolysiloxane (6 mm$^2$/second) | 6.0 |
| 2. Methylphenylpolyslioxane | 4.0 |
| 3. Mulberry orchid | 5.0 |
| 4. Dioctanoic acid neopentyl glycol | 3.0 |
| 5. Polyether..modified silicone (Note 1) | 3.0 |
| 6. Hydrophobically-treated fine titanium dioxide (Note 2) | 2.0 |
| 7. Magnesium sulfate | 0.7 |
| 8. Glycerin | 10.0 |
| 9. Antiseptic agent | Suitable amount |
| 10. Perfume | Suitable amount |
| 11. Purified water | Residual amount |

(Note 1)
Polyether-modified silicone: KF6012 (Shin-Etsu Chemical Co., Ltd.)
(Note 2)
Hydrophobically-treated fine titanium dioxide: Fine titanium dioxide of average particle diameter 0.05 um was dispersed in water to 10%, 10% sodium silicate solution ($SiO_2/NaO_2$) mole ratio: 0.5) equivalent to 2% relative to titanium dioxide in terms of $SiO_2$ was added, and the mixture thoroughly stirred. 10% aluminum sulfate solution equivalent to 7.5% relative to titanium dioxide in terms of $Al_2O_3$ was gradually added, andhydrates of silicic acid and alumina were thereby deposited on the surface of the titanium dioxide.

After the reaction, the mixture was filtered, rinsed and dried, and crushed in a jet mill. This was transferred to a Henschel mixer, 1% of the silicone compound obtained in Manufacturing Example 3 was added with vigorous stirring, and the mixture blended with stirring. Heat treatment was then performed at 120° C.

(Manufacturing Method)

A: Components 1-5 were heated and mixed, Component 6 was added and the mixture made homogeneous.

B: Components 7-9 and 11 were heated and dissolved.

C: B was gradually added to A with stirring to make an emulsion, cooled, and Component 10 was added to obtain a cream.

The cream obtained above had a fine texture, spread lightly, was non-tacky and non-oily, moist, fresh and had a cool freshness. It lasted well, did not change with temperature or time, and was extremely stable.

Example 38

Sunscreen Emulsion

| (Components) | (%) |
| --- | --- |
| 1. Decamethylcyclopentasiloxane | 20.0 |
| 2. Methylphenylpolysiloxane | 3.0 |
| 5. Monoisostearic acid sorbitan | 1.0 |
| 3. Polyether-modified silicone (Note 1) | 0.5 |
| 5. Trimethylsiloxy silicic acid | 1.0 |
| 6. Octyl p-methoxycinnamate | 4.0 |
| 7. Titanium dioxide (J) obtained in Example 8 | 8.0 |
| 8. Sorbitol | 2.0 |
| 9. Sodium chloride | 2.0 |
| 10. Antiseptic | Suitable amount |
| 11. Perfume | Suitable amount |
| 12. Purified water | Residual amount |

(Note 1)
Polyether-modified silicone: KF6015 (Shin-Etsu Chemical Co.,Ltd.)

(Manufacturing Method)

A: Components 1-6 were heated and mixed, Component 7 was added and the mixture made homogeneous.

B: Components 8-10 and 12 were dissolved uniformly.

C: B was gradually added to A with stirring to make an emulsion, cooled, and Component 11 was added to obtain an emulsion.

The sunscreen emulsion obtained above had a fine texture, spread lightly, was non-tacky and non-oily, moist and fresh. It lasted well, did not change with temperature or time, and was extremely stable.

Example 39

Liquid Foundation

| (Components) | (%) |
| --- | --- |
| 1. Decamethyl cyclopentasiloxane | 16.0 |
| 2. Dimethylpolysiloxane (6 mm$^2$/second) | 8.0 |
| 3. Octyl p-methoxycinnamate | 3.0 |
| 4. 12-hydroxystearic acid | 1.0 |
| 5. Fluorine-modified silicone (Note 1) | 15.0 |
| 6. Polyether-modified silicone (Note 2) | 5.0 |
| 7. Spherical silicone resin powder (Note 3) | 3.0 |
| 8. Fine titanium dioxide treated by silicone compound obtained in Manufacturing Example 1 | 8.0 |
| 9. Mica titanium treated by silicone compound obtained in Manufacturing Example 1 | 1.0 |
| 10. titanium dioxide treated by silicone compound obtained in Manufacturing Example 1 | 5.0 |
| 11. Red ocher treated by silicone compound obtained in Manufacturing Example 1 | 0.9 |
| 12. Yellow iron oxide treated by silicone compound obtained in Manufacturing Example 1 | 2.0 |
| 13. Black iron oxide treated with silicone obtained in Manufacturing Example 1 | 1.0 |
| 14. Ethanol | 15.0 |
| 15. Glycerin | 3.0 |
| 16. Magnesium sulfate | 1.0 |
| 17. Antiseptic | Suitable amount |
| 18. Perfume | Suitable amount |
| 19. Purified water | Residual amount |

(Note 1)
Fluorine-modified silicone: FL-100 (Shin-Etsu Chemical Co., Ltd.)
(Note 2)
Polyoxyethylene/trifluoropropyl co-modified silicone
(Note 3)
Spherical silicone resin powder: KMLP590 (Shin-Etsu Chemical Co., Ltd.)

(Manufacturing method)

A: Components 7-13 were mixed uniformly

B: Components 1-6 were heated to 70° C. with mixing, and A was added and uniformly dispersed.

C: Components 14-17 and 19 were heated to 40° C., B was gradually added to make an emulsion, cooled, and Component 18 was added to obtain a liquid foundation.

The foundation obtained above had a fine texture, spread lightly, was non-tacky and non-oily, clean and cool. It did not change with temperature or time, and was extremely stable.

Example 40

Eyeliner

| (Components) | (%) |
| --- | --- |
| 1. Decamethylcyclopentasiloxane | 22.0 |
| 2. Dimethylpolysiloxane (6 mm$^2$/second) | 5.0 |
| 3. Black iron oxide treated with silicone obtained in Manufacturing Example 4 | 20.0 |
| 4. Vitamin E acetate | 0.2 |
| 5. Jojoba oil | 2.0 |
| 6. Bentonite | 3.0 |
| 7. Polyether-modified silicone (Note 1) | 2.0 |
| 8. Ethanol | 10.0 |
| 9. 1,3-butylene glycol | 10.0 |
| 10. Antiseptic | Suitable amount |
| 11. Perfume | Suitable amount |
| 12. Purified water | Residual amount |

(Note 1)
Polyether-modified silicone: KF6017 (Shin-Etsu Chemical Co., Ltd.)

(Manufacturing Method)

A: Components 1-2, 4-7 were mixed, and Component 3 was added to give a uniform dispersion.

B: Components 8-10 and 12 were mixed.

C: B was gradually added to A, and Component 11 was added to obtain an eyeliner.

The eyeliner obtained above spread lightly, was easy to draw with, had a cool feel and was not tacky. It did not change with temperature or time, was extremely easy to use and very stable, had excellent water resistance and perspiration resistance, and lasted a very long time.

Example 41

Cream

| (Components) | (%) |
|---|---|
| 1. Decamethyl cyclopentasiloxane | 16.0 |
| 2. Dimethylpolysioxane (6 mm$^2$/second) | 4.0 |
| 3. Polyether-modified silicone (Note 1) | 5.0 |
| 4. POE (5) octyldodecyl ether (Note 2) | 1.0 |
| 5. Monostearic acid polyoxyethylene sorbitan (20E.O.) (Note 3) | 0.5 |
| 6. Anhydrous silicic acid-treated zinc oxide (Note 4) | 2.0 |
| 7. titanium dioxide composition (G) obtained in Example 5 | 10.0 |
| 8. Liquid paraffin | 2.0 |
| 9. Macadamia nut oil | 1.0 |
| 10. Ogon extract (Note 5) | 1.0 |
| 11. Gentiana extract (Note 6) | 0.5 |
| 12. Ethanol | Suitable amount |
| 13. 1,3-butylene glycol | 2.0 |
| 14. Antiseptic | Suitable amount |
| 15. Perfume | Suitable amount |
| 16. Purified water | Residual amount |

(Note 1) Polyether-modified silicone: KF6017 (Shin-Etsu Chemical Co., Ltd.)
(Note 2) POE (5) means that five polyoxyethylene units are joined together.
(Note 3) 20.E.O. means that twenty ethylene oxides are joined together.
(Note 4) Anhydrous silicic acid-treated zinc oxide: silica of particle size 0.01-10 micrometers including 50% zinc oxide (Sansufer SZ-5, Asahi Glass)
(Note 5) Ogon extract: extract with 50% 1,3-butylene glycol water
(Note 6) Gentiana extract: extract with 20% ethanol water (Manufacturing Method)

A: Components 1, 2, 3, 4 were mixed uniformly.

B: Components 1-5 were mixed, and A was added.

C: Components 10-14 and 16 were mixed, and B was added to form an emulsion.

D: C was cooled, and Component 15 was added to obtain a cream.

The cream obtained above was not tacky, spread lightly, had excellent skin contact with good cohesion, gave a lustrous finish and lasted very well. It did not change with temperature or time and was very stable.

Example 42

Foundation

| (Components) | (%) |
|---|---|
| 1. Decamethylcyclopentasioxane | 27.0 |
| 2. Methyiphenylpolysioxane | 3.0 |
| 3. Tri-isooctanoic acid glycerol | 10.0 |
| 4. Polyether-modified silicone (Note 1) | 1.0 |
| 5. Monoisostearic acid polyglyceryl | 3.0 |
| 6. Hydrophobically-treated mixed powder (Note 2) | 18.0 |
| 7. Red ocher | 1.2 |
| 8. Yellow iron oxide | 2.6 |
| 9. Black iron oxide | 0.2 |
| 10. 1,3-butylene glycol | 7.0 |
| 11. Sodium chloride | 0.5 |
| 12. Antiseptic | Suitable amount |
| 13. Perfume | Suitable amount |
| 14. Purified water | Residual amount |

(Note 1) Polyoxyalkylene/alkyl co-modified organopoly sioxane: KF6026 (Shin-Etsu Chemical Co.,Ltd.):
(Note 2) Hydrophobically-treated mixed powder
a. Fine titanium dioxide 8.0 (parts)
b. Fine zinc oxide 4.0
c. Talc 3.0
d. Mica 3.0

(Manufacturing Method)

A: Components a . . . d were mixed, the silicone compound produced in Manufacturing Example 1 was added to the mixed powder to 1%, and the result was heat-treated.

B: Components 1-5 were mixed, heated and dissolved, and Components 6-9 were uniformly dispersed.

C: Components 10-12 and 14 were mixed, and B was added to form an emulsion.

D: C was cooled, and Component 13 was added to obtain a foundation.

The cream obtained above was not tacky, spread lightly, had excellent skin contact with good cohesion, gave a lustrous finish and lasted very well. It did not change with temperature or time and was very stable.

Example 43

Suncut Cream

| (Components) | (%) |
|---|---|
| 1. Decamethyl cyclopentasioxane | 15.0 |
| 2. KP545 (Note 1) | 12.0 |
| 3. Triisooctanoic acid glyceryl | 5.0 |
| 4. Octyl p-methoxycinnamate | 6.0 |
| 5. KSG21 (Note 2) | 5.0 |
| 6. Polyether-modified silicone (Note 3) | 1.0 |
| 7. Zinc oxide composition (I) obtained in Example 7 | 20.0 |
| 8. Sodium chloride | 0.5 |
| 9. 1,3-butylene glycol | 2.0 |
| 10. Antiseptic | Suitable amount |
| 11. Perfume | Suitable amount |
| 12. Purified water | Residual amount |

(Note 1) KF-545: (Shin-Etsu Chemical Co.,Ltd.)
(Note 2) KSG21: (Shin-Etsu Chemical Co.,Ltd.)
(Note 3) Polyoxyalkylene/alkyl co-modified organopolysiloxane: KF6026 (Shin-Etsu Chemical Co.,Ltd.):

(Manufacturing Method)

A: Component 2 was added to part of Component 1 and uniformly blended, and Component 7 was added and dispersed by a bead mill.

B: 3-6 were mixed with the remainder of Component 1, and uniformly blended.

C: Components 8-10 and 12 were mixed and dissolved.

D: C was added to B to form an emulsion, and Component 11 was added to obtain a suncut cream.

The suncut cream obtained above was not tacky, spread lightly, had excellent skin contact with good cohesion, gave a lustrous finish, and lasted very well. It did not change with temperature or time and was very stable.

INDUSTRIAL FIELD OF APPLICATION

The powder composition of thee present invention has excellent dispersibility, and is suitable for cosmetics. The cosmetic material of this invention with which the powder composition and oil-based composition of this invention was blended, spread lightly, was not oily but moist and fresh, had a cool feel and lasted well. It did not change with temperature or time, was very stable and was an excellent cosmetic material.

The preceding examples can be repeated with similar success by substituting the generically or specifically described reactants and/or operating conditions of this invention for those used in the preceding examples.

The entire disclosures of all applications, patents and publications, cited herein and of corresponding Japanese Patent Application No. 2000-220892, filed Jul. 21, 2000, and International Application Serial No. PCT/JP01/06310, filed Jul. 19, 2001 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A powder composition comprising a powder and a silicone of formula (1)

wherein
R$^1$ are, each independently, an alkyl, aryl, aralkyl or fluorinated alkyl group having 1-30 carbon atoms,
R$^2$ is a group having one or more alcoholic hydroxy groups,
R$^3$ is of formula (2)

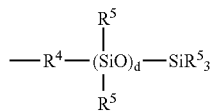

R$^4$ is oxygen,
R$^5$ are, each independently, an alkyl, aryl, aralkyl or fluorinated alkyl group having 1-30 carbon atoms or a hydroxyl group, and
$1.0 \leq a \leq 2.5$,
$0.001 \leq b \leq 1$,
$0.001 \leq c \leq 1$,
d is an integer of $0 \leq d \leq 500$, and
$1.5 \leq a+b+c \leq 2.6$.

2. A powder composition comprising a powder and a silicone of formula (1)

wherein
R$^1$ are, each independently, an alkyl, aryl, aralkyl or fluorinated alkyl group having 1-30 carbon atoms,
R$^2$ is of formula (4)

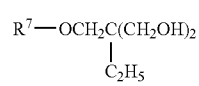

R$^7$ is a bifunctional hydrocarbon group,
R$^3$ is of formula (2)

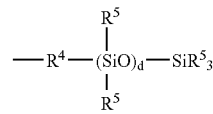

R$^4$ is an oxygen atom or a bifunctional hydrocarbon group,
R$^5$ are, each independently, an alkyl, aryl, aralkyl or fluorinated alkyl group having 1-30 carbon atoms or a hydroxyl group, and
$1.0 \leq a \leq 2.5$,
$0.001 \leq b \leq 1$,
$0.001 \leq c \leq 1$,
d is an integer of $0 \leq d \leq 500$, and
$1.5 \leq a+b+c \leq 2.6$.

3. A powder composition comprising a powder and a silicone of formula (1)

wherein
R$^1$ are, each independently, an alkyl, aryl, aralkyl or fluorinated alkyl group having 1-30 carbon atoms,
R$^2$ is of formula (5)

R$^7$ is a bifunctional hydrocarbon group,
R$^3$ is of formula (2)

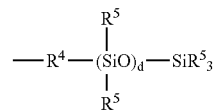

R$^4$ is an oxygen atom or a bifunctional hydrocarbon group,
R$^5$ are, each independently, an alkyl, aryl, aralkyl or fluorinated alkyl group having 1-30 carbon atoms or a hydroxyl group, and
$1.0 \leq a \leq 2.5$,
$0.001 \leq b \leq 1$,
$0.001 \leq c \leq 1$,
d is an integer of $0 \leq d \leq 500$, and
$1.5 \leq a+b+c \leq 2.6$.

4. The powder composition according to claim 3, wherein the silicone of formula (1) is more than 0.1 weight parts relative to 100 weight parts of the powder.

5. The powder composition according to claim 3, wherein the powder is zinc oxide.

6. The powder composition according to claim 3, wherein the powder is titanium dioxide.

7. The powder composition according to claim 3, wherein the powder is an extender pigment.

8. An oil-based powder dispersion, comprising the powder composition according to claim 3 dispersed in an oil.

9. A cosmetics material comprising a powder composition according to claim 3 and a cosmetically acceptable carrier.

10. A cosmetics material comprising an oil-based powder dispersion according to claim 8 and a cosmetically acceptable carrier.

11. The powder composition according to claim 2, wherein the silicone of formula (1) is more than 0.1 weight parts relative to 100 weight parts of the powder.

12. The powder composition according to claim 2, wherein the powder is zinc oxide.

13. The powder composition according to claim 2, wherein the powder is titanium dioxide.

14. The powder composition according to claim 2, wherein the powder is an extender pigment.

15. An oil-based powder dispersion, comprising the powder composition according to claim 2 dispersed in an oil.

16. A cosmetics material comprising a powder composition according to claim 2 and a cosmetically acceptable carrier.

17. A cosmetics material comprising an oil-based powder dispersion according to claim 16 and a cosmetically acceptable carrier.

18. A method of dispersing a powder in an oil, comprising adding a powder composition according to claim 3 to an oil.

19. A method of dispersing a powder in an oil, comprising adding a powder composition according to claim 2 to an oil.

20. The powder composition according to claim 1, wherein $R^2$ is of formula (3)

$$-R^6-OH \qquad (3)$$

wherein $R^6$ is a bifunctional hydrocarbon group.

21. The powder composition according to claim 2, wherein $R^4$ is oxygen.

22. The powder composition according to claim 3, wherein $R^4$ is oxygen.

* * * * *

UNITED STATES PATENT AND TRADEMARK OFFICE
CERTIFICATE OF CORRECTION

| | | |
|---|---|---|
| PATENT NO. | : 7,612,051 B2 | Page 1 of 1 |
| APPLICATION NO. | : 10/346176 | |
| DATED | : November 3, 2009 | |
| INVENTOR(S) | : Kamei et al. | |

It is certified that error appears in the above-identified patent and that said Letters Patent is hereby corrected as shown below:

On title page Item (57), line 16 reads "$1.0 \leq a \leq 2.5$, $0.01 \leq b \leq 1$, $0.001 \leq c \leq 1$, $1.5 \leq a+b+c \leq 2.6$, and"
should read -- $1.0 \leq a \leq 2.5$, $0.001 \leq b \leq 1$, $0.001 \leq c \leq 1$, $1.5 \leq a+b+c \leq 2.6$, and --.

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

PATENT NO.       : 7,612,051 B2
APPLICATION NO. : 10/346176
DATED            : November 3, 2009
INVENTOR(S)      : Kamei et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 774 days.

Signed and Sealed this

Nineteenth Day of October, 2010

David J. Kappos
*Director of the United States Patent and Trademark Office*